United States Patent [19]

Howard, III et al.

[11] Patent Number: 5,724,148
[45] Date of Patent: Mar. 3, 1998

[54] APPARATUS AND METHOD FOR DETERMINATION OF URINE COLOR

[75] Inventors: Willis Howard, III; Gary E. Rehm, both of Elkhart, Ind.

[73] Assignee: Bayer Corporation, Elkhart, Ind.

[21] Appl. No.: 647,120

[22] Filed: May 9, 1996

[51] Int. Cl.$^6$ ............................................... G01N 21/27
[52] U.S. Cl. ................................... 356/425; 356/402
[58] Field of Search ................................... 356/402, 405, 356/406, 408, 419, 425

[56] References Cited

U.S. PATENT DOCUMENTS

| | | | |
|---|---|---|---|
| 5,231,576 | 7/1993 | Suzuki et al. | 356/402 X |
| 5,303,037 | 4/1994 | Taranowski | 356/402 X |

*Primary Examiner*—Vincent P. McGraw
*Attorney, Agent, or Firm*—Roger N. Coe

[57] ABSTRACT

An apparatus for analyzing a body-fluid sample, such as a urine sample, disposed on a reagent pad is provided with means for illuminating the reagent pad on which the body-fluid sample is disposed, means for detecting light received from the reagent pad and generating a first reflectance signal at a first time and a second reflectance signal at a second time, and means for assigning a color to the body-fluid sample based upon the magnitudes of the first and second reflectance signals. The means for assigning the color to the body-fluid sample may include means for determining a pair of color coefficients each of which has a magnitude based upon the magnitudes of the reflectance signals and means for assigning the color to the body-fluid sample based upon the magnitudes of the color coefficients.

20 Claims, 6 Drawing Sheets

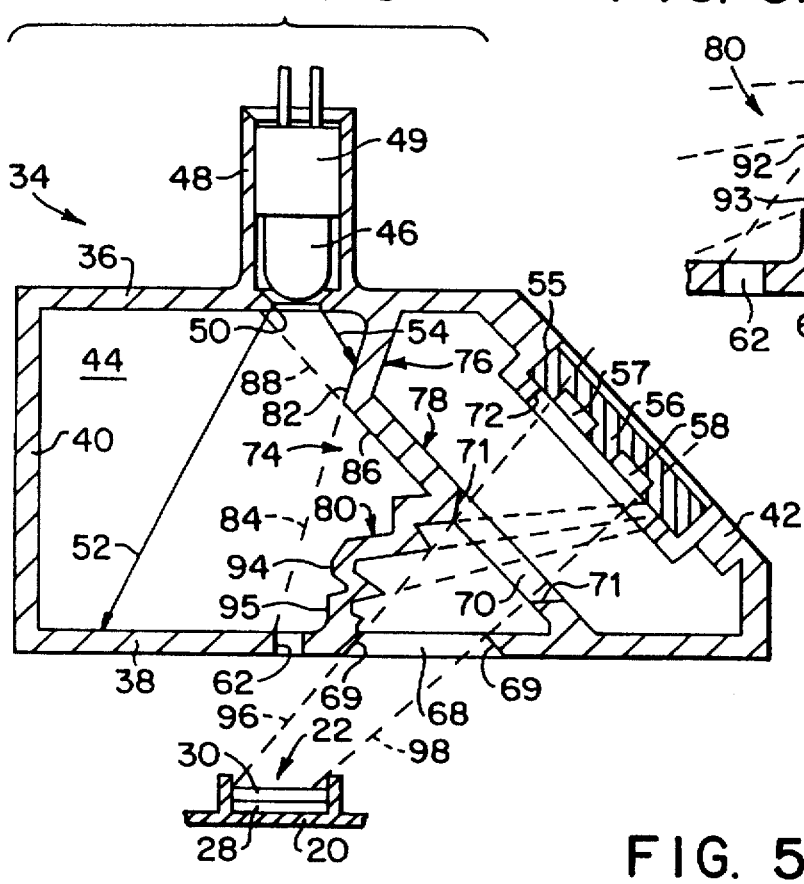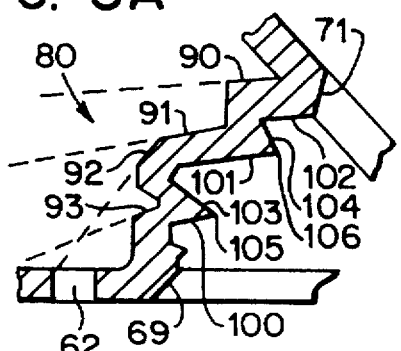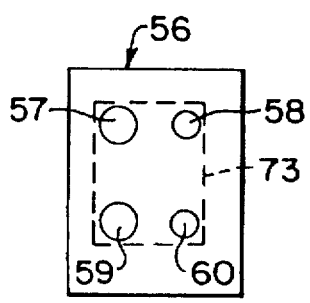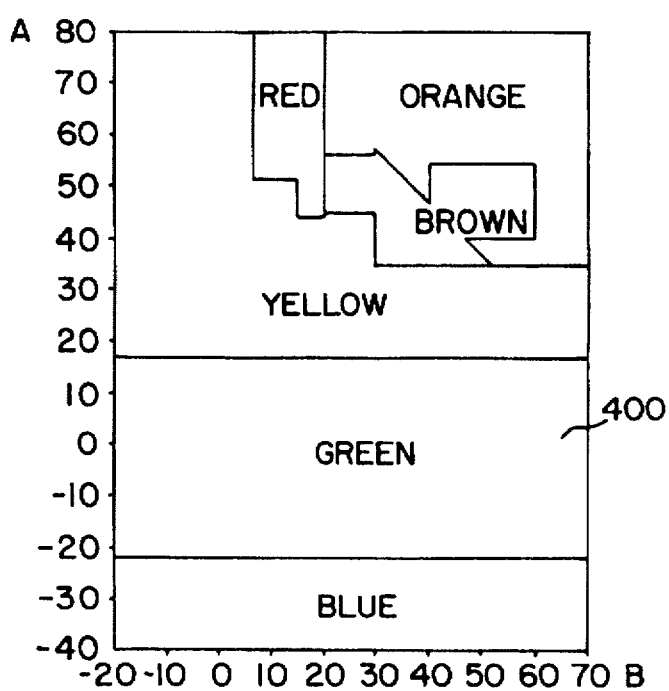

APPARATUS AND METHOD FOR DETERMINATION OF URINE COLOR

BACKGROUND OF THE INVENTION

The present invention relates to an apparatus and method for performing tests on a sample of body fluid to be analyzed, and more particularly to a reflectance spectroscope and method for the determination of urine color.

It is useful for various medical diagnostic purposes to utilize a reflectance spectroscope to analyze samples of body fluid, for example, to determine the color of a person's urine. A conventional reflectance spectroscope determines the color of a urine sample disposed on a white, non-reactive pad by illuminating the pad and taking a number reflectance readings from the pad, each having a magnitude relating to a different wavelength of visible light. The color of the urine on the pad is then determined based upon the relative magnitudes of the red, green and blue reflectance signals.

Conventional spectroscopes may be used to perform a number of different urinalysis tests utilizing a reagent strip on which a number of different reagent pads are disposed. Each reagent pad is provided with a different reagent which causes a color change in response to the presence of a certain type of constituent in urine, such as leukocytes (white blood cells) or red blood cells. Such a reagent strip may have ten different types of reagent pads.

SUMMARY OF THE INVENTION

The invention is directed to a method and apparatus for analyzing a body-fluid sample, such as a urine sample, disposed on a reagent pad. The apparatus is provided with means for illuminating the reagent pad on which the body-fluid sample is disposed, means for detecting light received from the reagent pad and generating a first reflectance signal at a first time and a second reflectance signal at a second time, and means for assigning a color to the body-fluid sample based upon the magnitudes of the first and second reflectance signals.

The detecting means may be composed of means for generating a reflectance signal in response to red light received from the reagent pad, means for generating a reflectance signal in response to green light received from the reagent pad, and means for generating a reflectance signal in response to blue light received from the reagent pad.

The means for assigning the color to the body-fluid sample may include means for determining a pair of color coefficients, each of which has a magnitude based upon the magnitudes of the reflectance signals, and means for assigning the color to the body-fluid sample based upon the magnitudes of the color coefficients.

The means for determining the color coefficients may be composed of means for determining a color correction factor based upon the magnitudes of the reflectance signals, means for assigning a weighting factor to the color correction factor, and means for determining the color coefficient based on the color correction factor and the weighting factor. The means for determining the color correction factor may include means for determining a pair of color correction values based upon the magnitudes of the reflectance signals and means for determining the difference between the two color correction values.

The invention is also directed to a method of analyzing a body-fluid sample disposed on a reagent pad. The method includes the steps of illuminating the reagent pad, detecting light received from the reagent pad at a first time and generating a first reflectance signal based on the detected light, detecting light received from the reagent pad at a second time and generating a second reflectance signal based on the detected light, and assigning a color to the body-fluid sample based upon the magnitudes of the first and second reflectance signals.

The method may include the steps of determining a pair of color coefficients, each having a magnitude based upon the magnitudes of the reflectance signals, and assigning the color to the body-fluid sample based upon the magnitudes of the color coefficients. The method may also include the steps of determining a color correction factor based upon the magnitudes of the reflectance signals, assigning a weighting factor to the color correction factor, and determining the first color coefficient based on the color correction factor and the weighting factor.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 3 is a cross-sectional view of a read head used in the spectroscope;

FIG. 3A is an enlarged view of a portion of the read head shown in FIG. 3;

FIG. 4 is a schematic view of a detector element used in the spectroscope;

FIG. 5 is a color coding chart utilized in connection with the spectroscope;

DETAILED DESCRIPTION OF A PREFERRED EMBODIMENT

Figure 1:
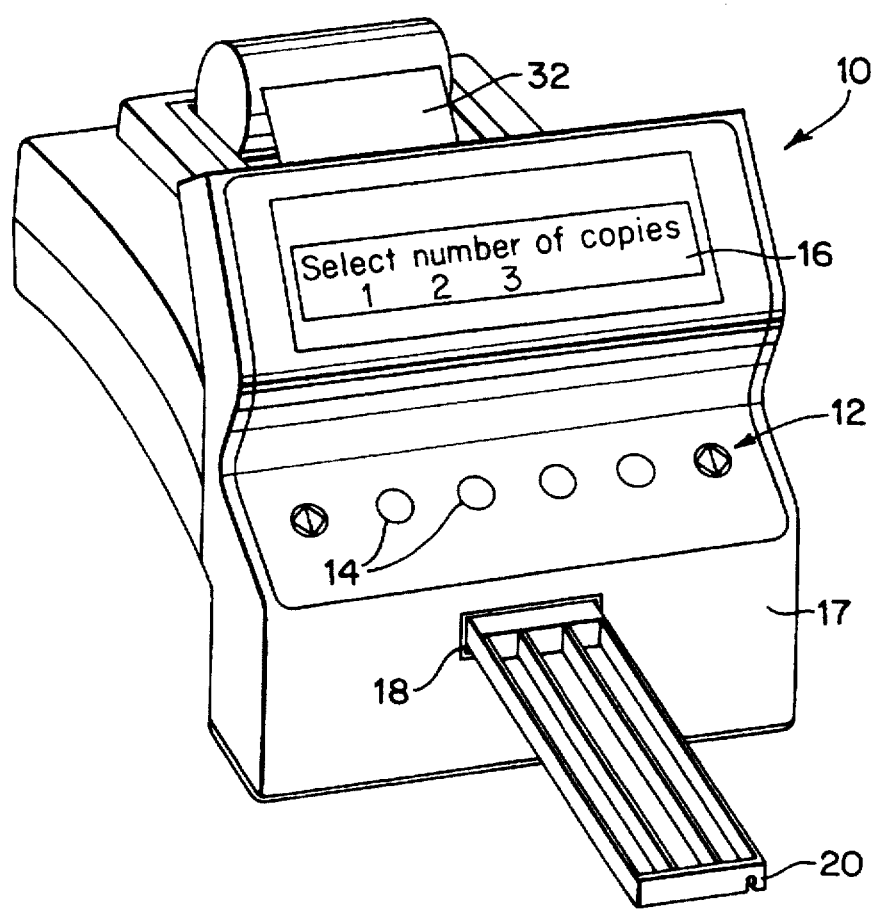
FIG. 1 is a perspective view of a reflectance spectroscope which may be used to perform various tests of a body fluid sample disposed on a reagent strip.
Figure 2:
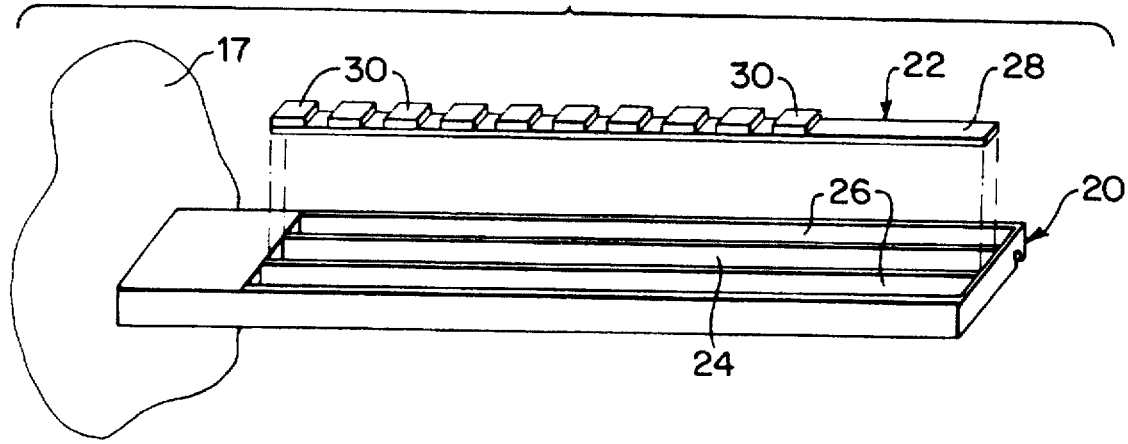
FIG. 2 is a perspective view of a reagent strip and a reagent tray used with the spectroscope of FIG. 1.

FIG. 1 illustrates a reflectance spectroscope 10 for performing various tests, such as urinalysis tests, on a reagent strip. The spectroscope 10 has an integral keyboard 12 with a number of entry keys 14 that may be depressed by the user. A visual display 16 for displaying various messages relating to the operation of the spectroscope 10 is disposed above the keyboard 12. Referring to FIGS. 1 and 2, the spectroscope 10 has a front face 17 with an opening 18 formed therein in which a tray 20 for carrying a reagent strip 22 is retractably disposed. The tray 20 has a central channel 24 and two side channels 26 formed therein, and the central channel 24 is sized to conform to the shape of the reagent strip 22.

The reagent strip 22 has a thin, non-reactive substrate 28 on which a number of reagent pads 30 are fixed. Each reagent pad 30 is composed of a relatively absorbent material impregnated with a respective reagent, each reagent and reagent pad 30 being associated with a particular test to be performed. When urinalysis tests are performed, they may include, for example, a test for leukocytes in the urine, a test of the pH of the urine, a test for blood in the urine, etc. When each reagent pad 30 comes into contact with a urine sample, the pad changes color over a time period, depending on the reagent used and the characteristics of the urine sample. The reagent strip 22 may be, for example, a Multistix® reagent strip commercially available from Bayer Corporation.

To perform urinalysis testing, the reagent strip 22 is dipped into a urine sample to be tested so that all of the reagent pads 30 are immersed in the sample. After the side of the reagent strip 22 is blotted to remove excess urine, the strip 22 is placed in the central channel 24 of the tray 20, and after the user presses one of the start keys 14 to initiate testing, the tray 20 is automatically retracted into the spectroscope 10.

A respective test is performed on each of the reagent pads 30 by illuminating a portion of the reagent pad 30 with white light from a light source and then determining the color of the reagent pad 30 based upon detection of light received from the illuminated portion of the reagent pad 30 at an angle (e.g. 45°) from the upper surface of the pad 30. After each test is performed, the tray 20 is repositioned relative to the light source so that the next reagent pad 30 to be tested is illuminated. When the testing is completed, the spectroscope 10 generates a record of the results, which are displayed on the display 16 and/or printed on a strip of paper 32 via a printer and/or sent to a computer.

Read Head

FIG. 3 is a cross-sectional view of an optical system, in the form of a read head 34, for illuminating portions of the reagent pads 30 and for detecting light from the reagent pads 30, and a portion of the tray 20 on which the reagent strip 22 is disposed. Referring to FIG. 3, the read head 34 has a housing with a top wall 36, a bottom wall 38, a side wall 40, an angled wall 42, a planar back wall 44, and a planar front wall (not shown) parallel to the back wall 44. An illumination source in the form of a light bulb 46 is supported directly above the reagent pad 30 to be tested via a cylindrical housing portion 48 integrally formed with the top wall 36.

The lower spherical portion of the light bulb 46 has a concentrating lens integrally formed therein, and the lower spherical surface is acid-etched to provide it with an uneven, diffusing surface so that the shape of the bulb filament does not contribute to non-uniformity of the emitted light. When manufactured, the bulb 46 is dynamically fitted to a ceramic base 49 when the bulb 46 is illuminated to ensure that the axial direction in which bulb 46 emits light is substantially parallel to the longitudinal axis of the ceramic base 49. The bulb 46 emits light through a circular aperture 50 formed in the top wall 36 to form a cone of light defined by a first edge ray 52 and a second edge ray 54.

The angled side wall 42 has a rectangular aperture 55 formed therein in which a rectangular detector array 56 is disposed. The detector array 56 has four reflectance detectors 57, 58, 59, 60 disposed therein (see FIG. 4), each of which is composed of a conventional colored or IR filter and a conventional silicon detector. Each filter allows light having a distinct wavelength to pass through so that each of the detectors 57–60 is responsive to light of a different wavelength range. The four wavelength bands of the filters are: 400–510 nm (nanometers) (blue); 511–586 nm (green); 587–660 nm (red); and 825–855 nm (infrared). Depending on the type of test being performed, one or more of the detectors 57–60 may be used.

Light passes through a first optical path from the light bulb 46, through a relatively small rectangular aperture 62 formed in the bottom wall 38, to illuminate a relatively small rectangular area of the reagent pad 30 being tested. The reagent pad 30 may be moved relative to the aperture 62 so that different rectangular areas of the reagent pad 30 are illuminated.

Light passes through a second optical path from the illuminated area on the reagent pad 30, through a first rectangular detection aperture 68 having angled edges 69 formed in the bottom wall 38, through a second rectangular detection aperture 70 having angled edges 71, and through a rectangular aperture 72 formed in the angled wall 42 to a detection area 73 (FIG. 4) in which the four detectors 57–60 are disposed.

The interior of the read head 34 is provided with an irregularly shaped baffle 74 composed of a first planar wall segment 76, a second planar wall segment 78, and a zig-zag shaped wall segment 80. The shape of the baffle 74 is designed to prevent singly-reflected light rays from reaching the reagent pad 30 from the light bulb 46 and to prevent singly-reflected light rays from reaching the detector area 73 from the reagent pad 30.

All surfaces of the baffle 74 and all interior surfaces of the housing walls 36, 38, 40, 42, 44 are shiny, specular surfaces so that any light incident upon any surface at an angle of incidence is reflected from that surface at an angle of reflection equal to the angle of incidence. This may be accomplished by injection-molding the read head 34 from a metal mold having highly polished molding surfaces. The read head 34 is preferably formed of black plastic so that only a small percentage of light, e.g. 5%, incident upon any of its internal surfaces is reflected. Consequently, any light that undergoes at least two reflections from any interior surfaces of the read head 34 is attenuated by at least 99.75%.

Referring to FIG. 3, the wall segment 76 has a specular surface 82 that is angled in a direction indicated by a dotted line 84, which intersects the bottom wall 38 at a point just to the left of the aperture 62. Consequently, any light rays emitted by the bulb 46 that impinge upon the surface 82 are reflected to an area to the left of the aperture 62. It should be noted that any such rays are reflected at least twice (in actuality at least three times) before they can pass through the aperture 62. It should also be noted that no light can be reflected from the surface 82 and pass directly through the aperture 62 without further reflection since the surface 82 is not visible when the interior of the read head 34 is viewed from the aperture 62.

The wall segment 78 has a specular surface 86 angled in a direction indicated by a dotted line 88, which intersects the top wall 36 at a point to the left of the circular opening 50 through which light passes. Consequently, there is no direct path from the light bulb 46 to the surface 86; therefore, any light that is reflected from the surface 86 to the aperture 62 will have undergone at least two (more than two in actuality) reflections from the interior surfaces of the read head 34.

FIG. 3A is an enlarged view of a portion of read head 34 shown in FIG. 3. Referring to FIGS. 3 and 3A, the zig-zag wall segment 80 has angled surfaces 90–93, each of which is angled in a direction indicated by a respective dotted line. Since all of the dotted lines intersect the bottom wall 38 or the side wall 40 to the left of the aperture 62, no light that impinges upon these surfaces 90–93 directly from the light bulb 46 can be reflected directly to the aperture 62. The zig-zag wall segment 80 has two further surfaces 94, 95 (FIG. 3) that are angled so that any light that impinges on those surfaces directly from the bulb 46 is reflected exclusively to the area of the bottom wall 38 to the right side of the aperture 62.

The only surfaces from which light rays emitted by the bulb 46 can be singly-reflected and still pass through the aperture 62 are the vertical walls of the aperture 62 itself. However, such singly-reflected light rays constitute an insignificant amount of the total light which passes directly from the light bulb 46 to the reagent pad 30 without reflection. There is also a singly-reflected light path from the bulb 46 to the walls 40 or 44 to the aperture 62. But because the bulb 46 concentrates light in a forward direction within the cone defined by rays 52 and 54, the amount of light going through the aperture 62 from this path is insignificant.

The second optical path, from the reagent pad 30 to the detector area 73 (FIG. 4), is generally indicated by a pair of dotted lines 96, 98. The side of the zig-zag wall segment 80 which is disposed adjacent the second optical path has a plurality of planar, specular surfaces 100, 101, 102 which are angled in a direction indicated by a number of corresponding dotted lines (shown in FIG. 3) which intersect the angled side wall 42 at a point to the lower right of the detector area 73. Consequently, any light rays that impinge upon these surfaces 100–102 directly from the reagent pad 30 without reflection cannot reach the detector area 73 without at least one more reflection, and thus any such light rays will be attenuated by at least 99.75%.

The side of the zig-zag wall segment 80 which is disposed adjacent the second optical path has a plurality of planar, specular surfaces 103,104 (FIG. 3A) which are angled so that no light rays from the reagent pad 30 can reach the surfaces 103, 104 directly without at least one reflection. Consequently, any light rays that impinge upon these surfaces 103–104 will already have undergone at least one reflection, and therefore any such light rays that eventually reach the detector area 73 will be reflected at least twice and thus be attenuated by at least 99.75%.

The wall surfaces 100 and 103 join at an edge 105, and the wall surfaces 101 and 104 join at an edge 106, the edges 105, 106 being substantially aligned with a respective edge of the detection area 73, and the edges 69, 71 of the detection apertures 68, 70 are aligned with the edges of the detection area 73.

Electronics

Figure 6:
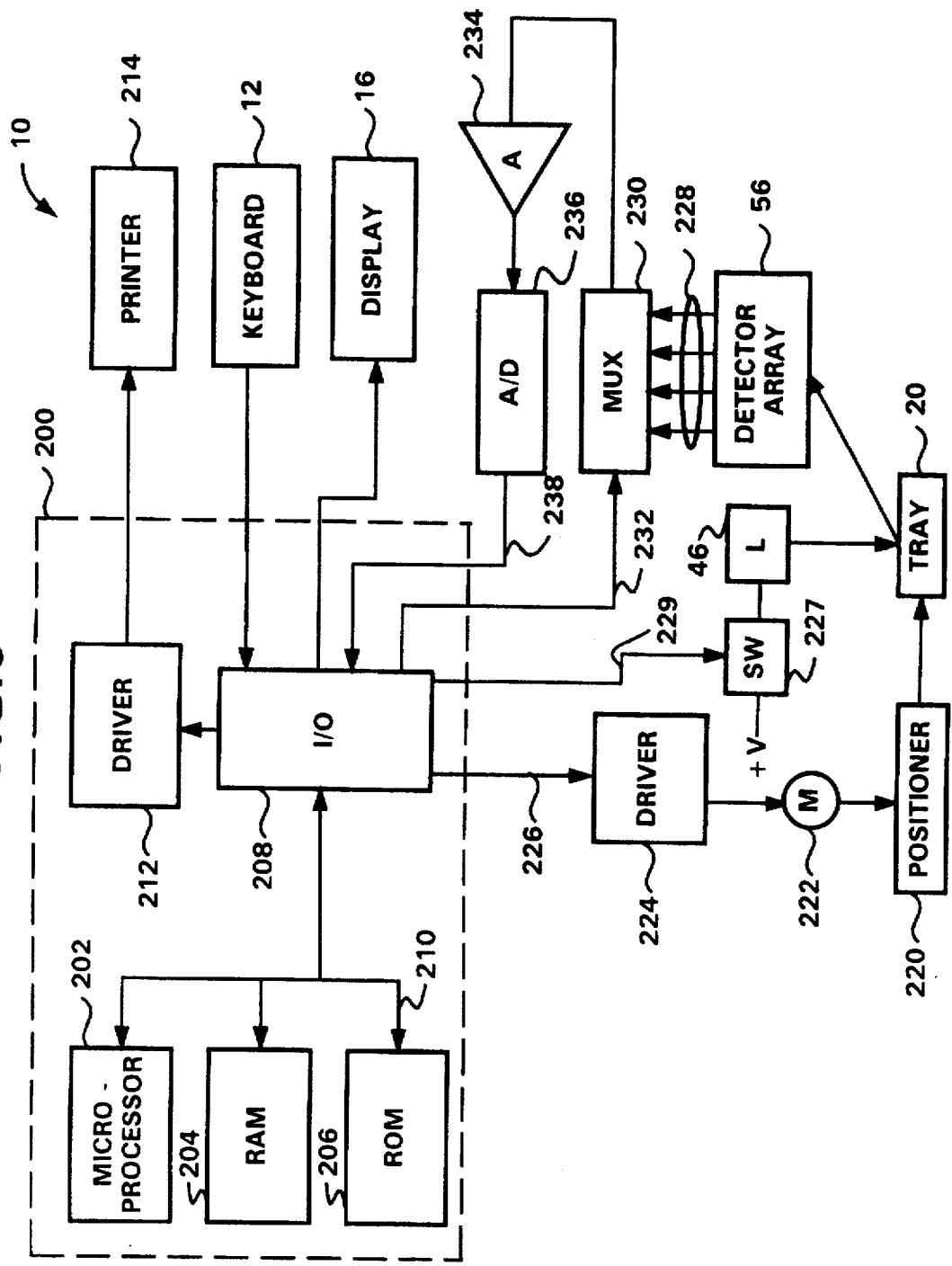
FIG. 6 is a block diagram of the electronics of the spectroscope of FIG. 1.

FIG. 6 is a block diagram of the electronics and other components of the spectroscope 10. Referring to FIG. 6, the operation of the spectroscope 10 is controlled by a microcontroller 200 which has a microprocessor 202, a random-access memory (RAM) 204, a read-only memory (ROM) 206, and an input/output (I/O) circuit 208, all of which are interconnected via an address/data bus 210. The microcontroller 200, which may be a conventional microcontroller such as a DS2253T microcontroller commercially available from Vallas Semiconductor, may incorporate a driver circuit 212 connected to the I/O circuit 208 for driving a printer 214.

The microcontroller 200 controls the movement of the reagent strip tray 20 via a conventional positioner 220 mechanically coupled to the tray 20 and a motor 222, such as a stepping motor, that is driven by drive signals generated by a driver circuit 224 connected to the I/O circuit 208 via an electrical line 226.

The microcontroller 200 selectively turns on the light bulb 46 via a switch 227 connected to the I/O circuit 208 via an electrical line 229. The light bulb 46 is turned on one second prior to the performance of a test so that it will be sufficiently warmed up. If the light bulb 46 is not needed to provide illumination within the next one-second period following a test, it is turned off to conserve its life.

Each of the detectors 57–60 of the detector array 56 may generate an electrical reflectance signal on one of a number of electrical lines 228. Each reflectance signal has a magnitude that depends on the amount of light detected by the associated detector. The microcontroller 200 can selectively read any one of the reflectance signals by transmitting a select signal to a multiplexer 230 via a line 232. The multiplexer 230 then transmits the selected reflectance signal to an amplifier 234 and an analog-to-digital (A/D) converter 236, which transmits the binary signal corresponding to the analog reflectance signal output by the amplifier 234 to the microcontroller 200 via a line 238 connected to the I/O circuit 208.

Operation

Figure 7A:
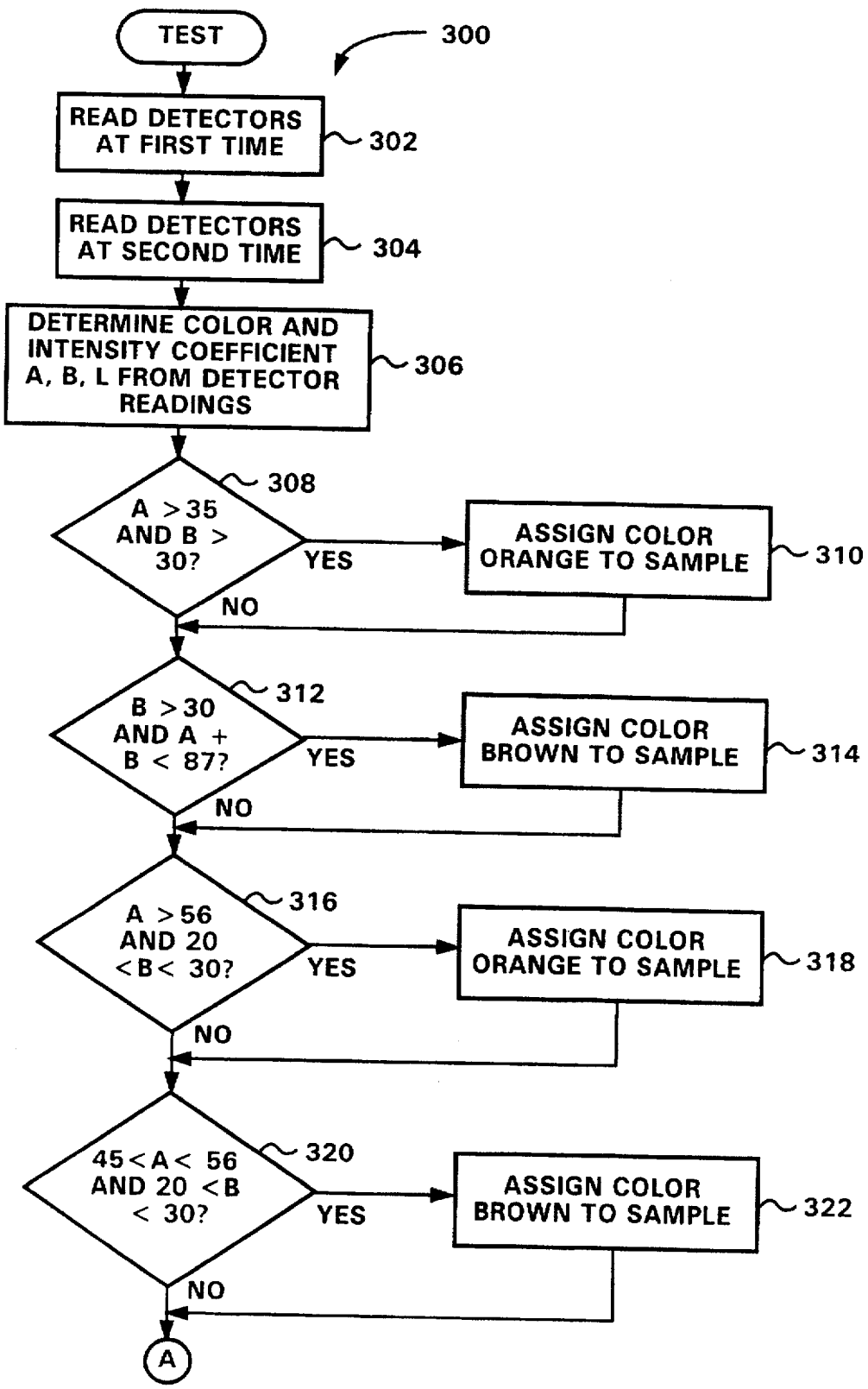
FIGS. 7A-7C are a flowchart of a test routine that may be used to determine the color of a urine sample on a reagent pad.
Figure 7B:
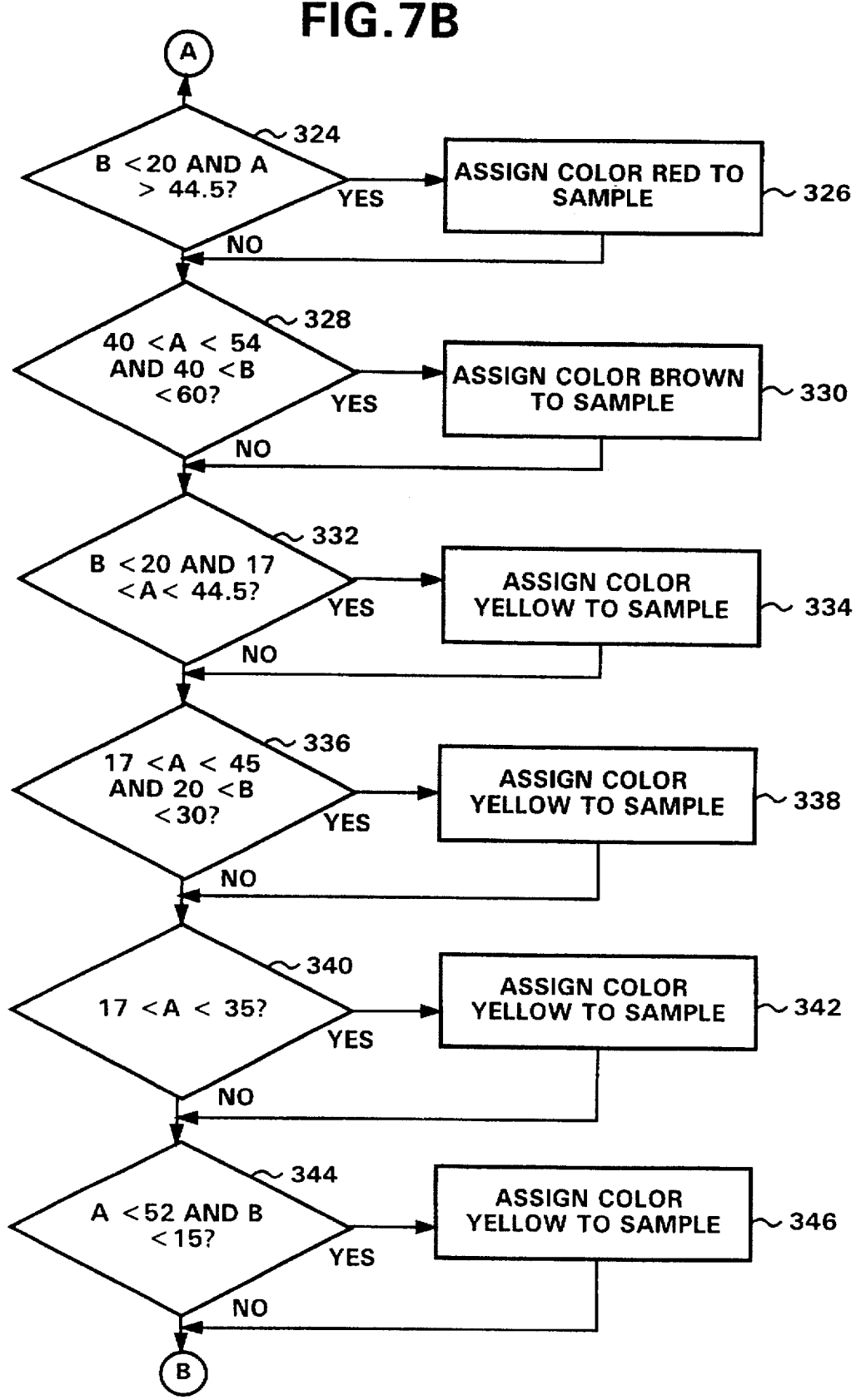
Figure 7C:
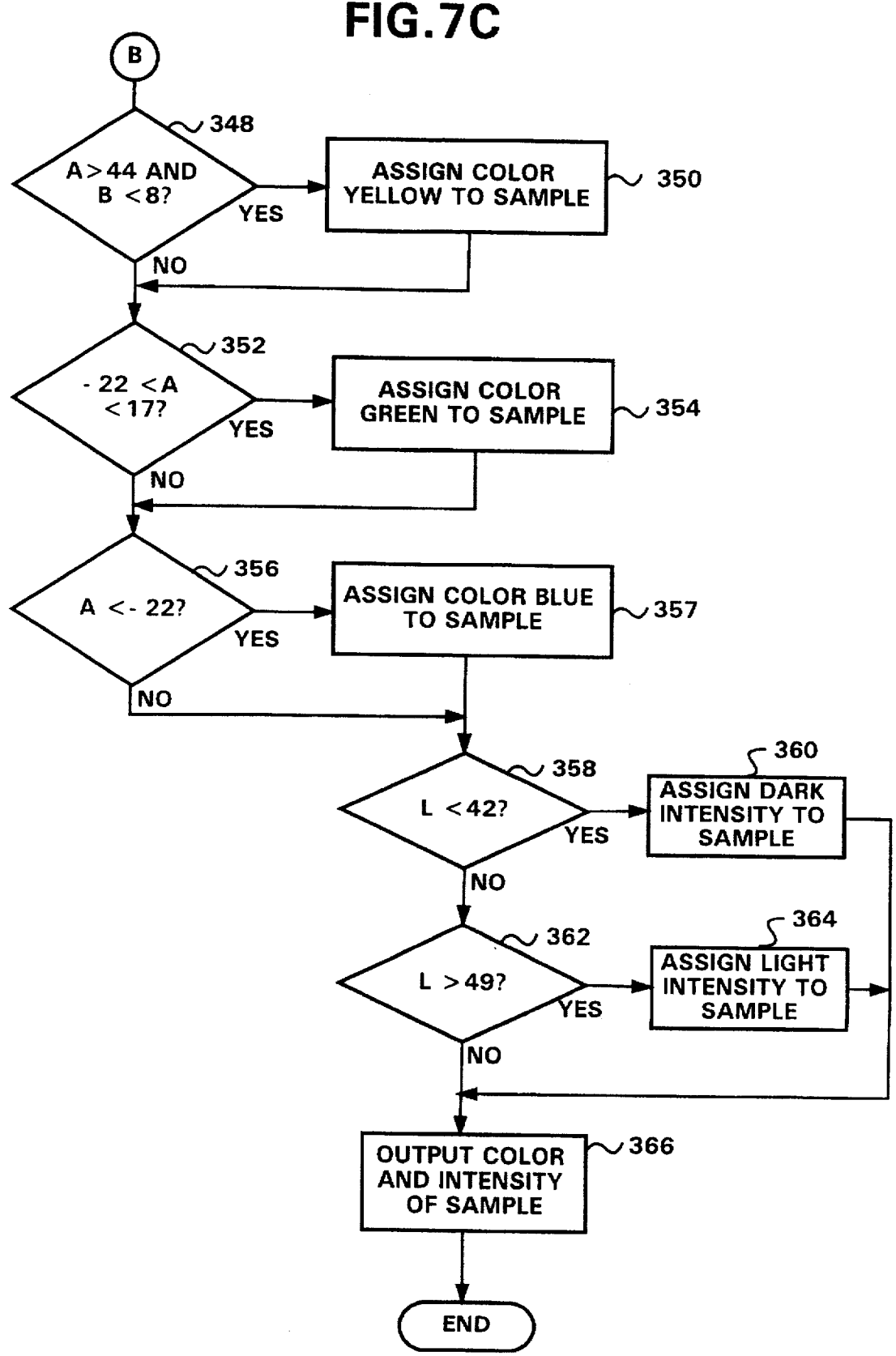

The operation of the spectroscope 10 is controlled by a computer program stored in the ROM 206 and executed by the microprocessor 202. A flowchart of a test routine 300 for making a determination of the color of a urine sample is shown in FIGS. 7A–7C. When the test is performed, the reagent pad 30 having the reagent which changes color in response to the presence of leukocytes is positioned directly below the light bulb 46. By using that reagent pad 30 to perform both the leukocyte test and the urine color determination, the need for an additional white, non-reactive pad 30 to be disposed on the reagent strip 22 for the urine color determination is eliminated.

Referring to FIG. 7A, at step 302, while the reagent pad 30 utilized for the leukocyte test is illuminated, each of the four detectors 57–60 is "read" at a first time by transmitting each of the reflectance signals generated by the detectors 57–60 through the multiplexer 230 to the amplifier 234, the A/D converter 236, the I/O circuit 208, and the RAM 204 where their values are stored.

For example, the first time the detectors 57–60 are read may be fifteen seconds after the reagent strip 22 is dipped in the urine sample by the operator. As soon as the reagent strip 22 is immersed in the urine sample, the operator pushes one of the keys 14 (FIG. 1), which starts an internal timer (not shown) in the spectroscope 10. When the timer reaches the first predetermined time, the detectors 57–60 are read at step 302. At step 304, each of the detectors 57–60 is read at a second, subsequent time, such as 60 seconds after the reagent strip 22 is immersed in the urine sample.

At step 306, based on the reflectance readings made during steps 302, 304, the spectroscope 10 determines a number of coefficients, including a color coefficient A, a color coefficient B, and an intensity coefficient L. As used herein, the term "intensity" refers to how light or dark the urine sample is, such as light yellow or dark yellow. The coefficients determined at step 306 are set forth below:

$$A = C_a(R_1 + W_a F) - (G_1 + W_b F) \quad [1]$$

$$B = C_b(G_1 + W_b F) - (B_1 + W_c F) \quad [2]$$

$$L = B_1 + W_c F \quad [3]$$

where $C_a$ and $C_b$ are constants; $R_1$, $B_1$, $G_1$ are the values (in percent reflectance, e.g. for $R_1$ of 50% reflectance, the $R_1$ value would be 50) of the reflectance signals generated at the first time by the red, blue and green detectors, respectively; $W_a$, $W_b$, $W_c$ are weighting factors; and F is a color correction factor that is used to provide a color correction to eliminate the effects of the color change of the reagent pad 30 due to the pad reacting to the leukocytes in the urine sample. The color correction factor F may be in accordance with the following equation:

$$F = G_1 I_1 - G_2 I_2 \qquad [4]$$

where $G_1$ and $G_2$ are the values (in percent reflectance) of the reflectance signals generated by the green detector at the first and second times, respectively, and where $I_1$ and $I_2$ are the values of the reflectance signals (in percent reflectance) generated by the infrared detector at the first and second times, respectively.

The color correction factor F is based upon the recognition that the color change of the reagent pad 30 due to the presence of leukocytes (which color change is unrelated to the original color of the urine sample) most strongly affects the green light received from the reagent pad 30 (when the Bayer reagent strip noted above is used, the presence of leukocytes causes the reagent pad 30 to continuously change in color, over a period of time from immersion to about two minutes after immersion, from white to a shade of tan, which depends on the leukocyte concentration present). Thus, a relatively large difference between $G_1$ and $G_2$ signifies a relatively large color change due to the presence of leukocytes, and a relatively small difference between $G_1$ and $G_2$ signifies a relatively small color change due to the presence of leukocytes. Where urine color (or the color of another body-fluid sample) is to be determined for reagent pads normally used for tests other than leukocyte testing, the color change due to the reaction between the reagent and the blood constituents being tested may most strongly affect a color band other than green.

Different weighting factors $W_a$, $W_b$, $W_c$ are used because the color effects due to the presence of leukocytes may unequally affect the three color bands sensed by the red, blue and green detectors, i.e. the presence of leukocytes may affect the reflectance signal generated by the red detector more strongly than it does the signal generated by the blue detector. The $I_1$ and $I_2$ infrared values in the color correction factor F, which do not substantially change in response to the color change due to the presence of leukocytes, act as error correction values to compensate for slight color variations due to slight nonuniformities from reagent pad to reagent pad and from reagent (manufacturing) lot to reagent lot.

The magnitude of the intensity coefficient L defined above is based primarily upon the amount of blue light received by the blue detector. This is based on the recognition that the magnitude of the blue light emitted by the reagent pad 30 is most strongly correlated with the lightness or darkness of the urine sample as visually perceived.

An example of one set of coefficients which may be used are set forth below:

$$A = 5[R_1 + 40(G_1 I_1 - G_2 I_2)] - [G_1 + 64(G_1 I_1 - G_2 I_2)] \qquad [5]$$

$$B = 2[G_1 + 64(G_1 I_1 - G_2 I_2)] - [B_1 + 24(G_1 I_1 - G_2 I_2)] \qquad [6]$$

$$L = B_1 + 24(G_1 I_1 - G_2 I_2) \qquad [7]$$

Other formulations for the coefficients may be used, depending upon the type of test, e.g. leukocyte test, during which the body-fluid sample color is to be determined and the type of reagent pad and reagent strip used.

After the color coefficients A, B are determined at step 306, they are used to assign a color to the color sample at steps 308–356 of FIGS. 7A–7C. The color is assigned by comparing the color coefficients A and B with various predetermined ranges and thresholds, which are empirically determined during the design phase of the spectroscope 10, as described below.

The ranges and thresholds utilized in steps 308–356 are determined by visually inspecting a relatively large number of urine samples, e.g. in excess of 100, of many different colors and intensities, such as red, orange, light yellow, dark yellow, green and blue, when the samples are disposed in clear, colorless test tubes. After each sample is visually inspected and manually assigned a color based on the visual inspection, steps 302–306 described above are performed on the urine sample to calculate the two color coefficients A and B.

Then, on a color coding chart like the one shown in FIG. 5, with the Y-axis representing the range of the color coefficient A and the X-axis representing the range of the color coefficient B, each urine sample is represented by a point on the chart (the point being positioned based upon the color coefficients A, B of the sample) and a designation of the visually determined color of the urine sample represented by the point. After all the points for the urine samples are located, it will be apparent that similar colors of urine samples will be grouped together in various areas, the boundaries of which can be visually determined. For example, as shown in FIG. 5, a rectangular area 400 represents the area in which substantially all green urine samples were located (based on their color coefficients A and B).

After the boundaries are determined, then the ranges and thresholds of steps 308–356 are determined so that all urine samples subsequently analyzed by the spectroscope 10 are assigned the color of the area in which the sample is located in the color coding chart, based upon the color coefficients A, B of the sample.

Referring to FIG. 7A, at step 308, if the color coefficient A is greater than 35 and the color coefficient B is greater than 30, the program branches to step 310 where the color orange is assigned to the urine sample, the color assignment being stored in the RAM 204. It should be noted that this color assignment is an initial assignment which may (or may not) be changed by a subsequent step in the program. Referring also to FIG. 5, the test at step 308 (A>35 and B>30) corresponds to a rectangular area in the color coding chart. It should be noted that this rectangular area is partially overlapped by areas designated brown and yellow. Thus, a urine sample having coefficients A and B which correspond to one of these overlapped areas would be initially assigned the color orange, and then that initial assignment would subsequently be changed to brown or yellow.

Referring to FIG. 7A, at step 312, if the coefficient B is greater than 30 and the sum of the coefficients A and B is less than 87, the program branches to step 314, where the color brown is assigned to the sample. At step 316, if the coefficient A is greater than 56 and the coefficient B is between 20 and 30, the program branches to step 318, where the color orange is assigned to the sample. At step 320, if the coefficient A is between 45 and 56 and the coefficient B is between 20 and 30, the program branches to step 322, where the color brown is assigned to the sample.

Referring to FIG. 7B, at step 324, if the coefficient B is less than 20 and the coefficient A is greater than 44.5, the program branches to step 326, where the color red is assigned to the sample. At step 328, if the coefficient A is between 40 and 54 and the coefficient B is between 40 and 60, the program branches to step 330, where the color brown is assigned to the sample. At step 332, if the coefficient B is less than 20 and the coefficient A is between 17 and 44.5, the program branches to step 334, where the color yellow is assigned to the sample. At step 336, if the coefficient A is between 17 and 45 and the coefficient B is between 20 and 30, the program branches to step 338, where the color yellow is assigned to the sample. At step 340, if the coefficient A is between 17 and 35, the program branches to step 342, where the color yellow is assigned to the sample. At step 344, if the coefficient A is less than 52 and the coefficient B is less than 15, the program branches to step 346, where the color yellow is assigned to the sample.

Referring to FIG. 7C, at step 348, if the coefficient A is greater than 44 and the coefficient B is less than 8, the program branches to step 350, where the color yellow is assigned to the sample. At step 352, if the coefficient A is between −22 and 17, the program branches to step 354, where the color green is assigned to the sample. At step 356, if the coefficient A is less than −22, the program branches to step 357, where the color blue is assigned to the sample.

Steps 358–364 are performed to assign an intensity to the urine sample based on the magnitude of the intensity coefficient L determined at step 306 (FIG. 7A). At step 358, if the intensity coefficient L is less than 42, the program branches to step 360 where a dark intensity is assigned to the sample. At step 362, if the intensity coefficient L is greater than 49, the program branches to step 360 where a light intensity is assigned to the sample (if the intensity coefficient L is between 42 and 49, no intensity is assigned to the sample since it is of medium intensity).

At step 366, the color and intensity (if any) assigned to the urine sample, e.g. light yellow or dark yellow, is output, such as by generating a printed record of the color and intensity and/or displaying the color and intensity on the visual display 16. It should be understood that the particular manner of assigning color and intensity to urine samples described above is not critical to the invention, and that numerous other ways could be utilized.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent of the United States is:

1. An apparatus for analyzing a urine sample disposed on a reagent pad having a color which changes over time in response to said urine sample, said apparatus comprising:

means for illuminating said reagent pad on which said urine sample is disposed;

first means for detecting light of a first color received from said reagent pad and generating a first reflectance signal at a first time when said color of said reagent pad is changing and a second reflectance signal at a second time when said color of said reagent pad is changing, said second time being subsequent to said first time and each of said first and second reflectance signals having a magnitude;

second means for detecting light of a second color received from said reagent pad and generating a third reflectance signal when said color of said reagent pad is changing, said third reflectance signal having a magnitude;

third means for detecting light of a third color received from said reagent pad and generating a fourth reflectance signal when said color of said reagent pad is changing, said fourth reflectance signal having a magnitude;

means for determining a first color coefficient having a magnitude based upon said magnitudes of said first, second and third reflectance signals;

means for determining a second color coefficient having a magnitude based upon said magnitudes of said first, second and fourth reflectance signals; and means for assigning a color to said urine sample based upon said magnitudes of said first and second color coefficients.

2. An apparatus as defined in claim 1 wherein said first means comprises a detector for generating said first and second reflectance signals in response to green light received from said reagent pad.

3. An apparatus as defined in claim 1 wherein said second means comprises a detector for generating said third reflectance signal in response to red light received from said reagent pad.

4. An apparatus as defined in claim 1 wherein said third means comprises a detector for generating said fourth reflectance signal in response to blue light received from said reagent pad.

5. An apparatus as defined in claim 1 wherein said means for determining said first color coefficient comprises:

means for determining a color correction factor based upon said magnitudes of said first and second reflectance signals;

means for assigning a weighting factor to said color correction factor; and means for determining said first color coefficient based on said color correction factor, said weighting factor, and said magnitude of said third reflectance signal.

6. An apparatus as defined in claim 5 wherein said means for determining said color correction factor comprises:

means for determining a first color correction value based upon said magnitude of said first reflectance signal;

means for determining a second color correction value based upon said magnitude of said second reflectance signal; and means for determining the difference between said first color correction value and said second color correction value.

7. An apparatus as defined in claim 6 wherein said means for determining said first color correction value comprises means for dividing said magnitude of said first reflectance signal by a first error correction factor and wherein said means for determining said second color correction value comprises means for dividing said magnitude of said second reflectance signal by a second error correction factor.

8. An apparatus as defined in claim 7 additionally comprising means for detecting infrared light received from said reagent pad and generating a first infrared reflectance signal having a magnitude at a first time and a second infrared reflectance signal having a magnitude at a second time, said second time being subsequent to said first time and wherein said first error correction factor comprises said magnitude of said first infrared reflectance signal and wherein said second error correction factor comprises said magnitude of said second infrared reflectance signal.

9. An apparatus as defined in claim 1 wherein said means for determining said first color coefficient comprises:

means for determining a color correction factor based upon said magnitudes of said first and second reflectance signals;

means for assigning a first weighting factor to said color correction factor;

means for assigning a second weighting factor to said color correction factor; and means for determining said first color coefficient based on the product of said first weighting factor and said color correction factor, the product of said second weighting factor and said color correction factor, said magnitude of a first of said reflectance signals, and said magnitude of a second of said reflectance signals.

10. An apparatus for analyzing a body-fluid sample disposed on a reagent pad, said apparatus comprising:

means for illuminating said reagent pad on which said body-fluid sample is disposed;

means for detecting light received from said reagent pad and generating a first reflectance signal at a first time and a second reflectance signal at a second time, said second time being subsequent to said first time and each of said first and second reflectance signals having a magnitude; and means for assigning a color to said body-fluid sample based upon said magnitudes of said first and second reflectance signals.

11. An apparatus as defined in claim 10 wherein said detecting means comprises:

means for generating a reflectance signal in response to red light received from said reagent pad;

means for generating a reflectance signal in response to green light received from said reagent pad; and means for generating a reflectance signal in response to blue light received from said reagent pad.

12. An apparatus as defined in claim 10 wherein said means for assigning said color to said body-fluid sample comprises:

means for determining a first color coefficient having a magnitude based upon said magnitudes of said reflectance signals;

means for determining a second color coefficient having a magnitude based upon said magnitudes of said reflectance signals; and means for assigning said color to said body-fluid sample based upon said magnitudes of said first and second color coefficients.

13. An apparatus as defined in claim 12 wherein said means for determining said first color coefficient comprises:

means for determining a color correction factor based upon said magnitudes of said first and second reflectance signals;

means for assigning a weighting factor to said color correction factor; and means for determining said first color coefficient based on said color correction factor and said weighting factor.

14. An apparatus as defined in claim 13 wherein said means for determining said color correction factor comprises:

means for determining a first color correction value based upon said magnitude of said first reflectance signal;

means for determining a second color correction value based upon said magnitude of said second reflectance signal; and means for determining the difference between said first color correction value and said second color correction value.

15. An apparatus as defined in claim 14 wherein said means for determining said first color correction value comprises means for dividing said magnitude of said first reflectance signal by a first error correction factor and wherein said means for determining said second color correction value comprises means for dividing said magnitude of said second reflectance signal by a second error correction factor.

16. A method of analyzing a body-fluid sample disposed on a reagent pad, said method comprising the steps of:

(a) illuminating said reagent pad;

(b) detecting light received from said reagent pad at a first time;

(c) generating a first reflectance signal based on said light detected during said step (b), said first reflectance signal having a magnitude;

(d) detecting light received from said reagent pad at a second time subsequent to said first time;

(e) generating a second reflectance signal based on said light detected during said step (d), said second reflectance signal having a magnitude; and (f) assigning a color to said body-fluid sample based upon said magnitudes of said first and second reflectance signals.

17. A method as defined in claim 16 wherein said step (f) comprises the steps of:

(f1) determining a first color coefficient having a magnitude based upon said magnitudes of said reflectance signals;

(f2) determining a second color coefficient having a magnitude based upon said magnitudes of said reflectance signals; and (f3) assigning said color to said body-fluid sample based upon said magnitudes of said first and second color coefficients.

18. A method as defined in claim 17 wherein said step (f1) comprises the steps of:

(f4) determining a color correction factor based upon said magnitudes of said first and second reflectance signals;

(f5) assigning a weighting factor to said color correction factor; and (f6) determining said first color coefficient based on said color correction factor and said weighting factor.

19. A method as defined in claim 18 wherein said step (f4) comprises the steps of:

(f7) determining a first color correction value based upon said magnitude of said first reflectance signal;

(f8) determining a second color correction value based upon said magnitude of said second reflectance signal; and (f9) determining the difference between said first color correction value and said second color correction value.

20. A method as defined in claim 19 wherein said step (f7) comprises the step of dividing said magnitude of said first reflectance signal by a first error correction factor and wherein said step (f8) comprises the step of dividing said magnitude of said second reflectance signal by a second error correction factor.

* * * * *